May 25, 1954 H. C. SWIM Plant Pat. 1,280
ROSE PLANT
Filed March 17, 1953
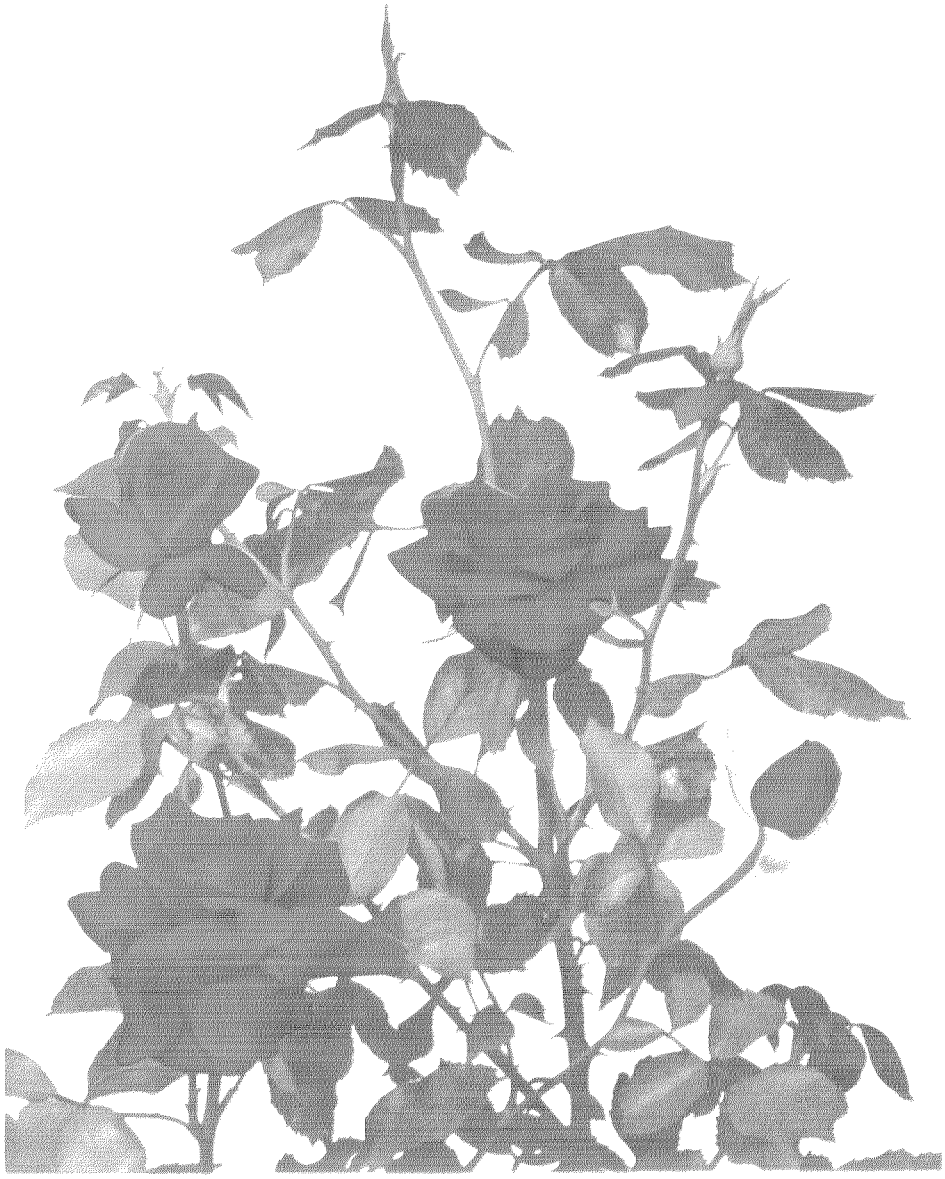
Inventor.
H. C. Swim
By: Robb & Robb
Attorneys Patented May 25, 1954

Plant Pat. 1,280

UNITED STATES PATENT OFFICE 1,280

ROSE PLANT

Herbert C. Swim, Ontario, Calif., assignor to Armstrong Nurseries, Inc., Ontario, Calif., a corporation of California Application March 17, 1953, Serial No. 343,009

1 Claim. (Cl. 47—61)

The present invention relates to a new and distinct variety of rose plant of the hybrid tea class, which was originated by me by crossing the well-known variety "Charlotte Armstrong" (Plant Patent No. 455) with the variety "Floradora" (unpatented).

The primary objective in making this cross was to produce a new variety of rose plant which combines the best characteristics of the two parent varieties. This objective was fully achieved, as evidenced by the fact that my new variety is endowed with the following unique combination of outstanding characteristics:

(1) The cluster blooming habit corresponding to that of the pollen parent "Floradora";

(2) The long individual flowering stems which is a characteristic of the seed parent "Charlotte Armstrong";

(3) The relatively large size of the blooms approaching that of "Charlotte Armstrong";

(4) The abundance of bloom production throughout the growing season, approaching that of "Floradora";

(5) The good petal substance approaching that of "Floradora," with attendant long-lasting quality of the flowers, which is also typical of "Floradora"; and (6) The dark green, glossy foliage typical of "Floradora," but produced in the size and abundance that is typical of "Charlotte Armstrong."

In comparison with its seed parent, "Charlotte Armstrong," the color of the blooms of my new variety is a much deeper shade of red, as distinguished from the light shade of red that is characteristic of the blooms of "Charlotte Armstrong," and which are more popularly described as Spectrum Red to Cerise in color. The blooms of my new variety are usually borne in clusters, whereas those of "Charlotte Armstrong" are usually borne singly; the blooms of my new variety have a more pronounced fragrance than those of "Charlotte Armstrong"; and the foliage of my new variety is glossy, in contrast to the non-glossy foliage of "Charlotte Armstrong."

As compared with its pollen parent, "Floradora," the blooms of my new variety are also a deeper shade of red, instead of the lighter shade of red that is so characteristic of "Floradora" and which is usually considered as Scarlet-Red with Nopal Red on the reverse of the petals, these latter colors showing a strong influence of orange; the blooms of my new variety are much larger in size than those of "Floradora"; the flowering stems of my new variety are substantially longer than those of this parent; and the foliage of my new variety is substantially larger than that of "Floradora."

Asexual reproduction of my new variety by budding at Ontario, California, shows that the foregoing characteristics and distinctions come true to form and are established and transmitted through succeeding propagations.

The accompanying drawing shows typical specimens of the flowers, foliage and stems of my new variety, with the colors thereof depicted as nearly true as it is reasonably possible to make the same in an illustration of this character.

The following is a detailed description of my new variety, with color terminology in accordance with Robert F. Wilson's Horticultural Colour Chart (hereinafter identified as "Wilson") and with Ridgway's Color Standards and Nomenclature (hereinafter identified as "Ridgway");

Type: Bush; outdoor; seedling; for cut flowers and for garden decoration.

Class: Hybrid tea.

Breeding: Seedling.

*Seed parent.*—"Charlotte Armstrong."

*Pollen parent.*—"Floradora."

Propagation: Holds its distinguishing characteristics through succeeding propagations by budding.

*Flower*

Locality where grown and observed: Ontario, California.

Flowers borne: Sometimes singly; usually 3 or 4 or more to stem, the stems of each bloom in the cluster being much longer than average; on strong, long individual stems.

Quantity of bloom: Abundant, outdoors.

Continuity: Nearly continuous during growing season.

Frangrance: Penetrating; tea.

Bud:

*Peduncle.*—Average length; average caliper; erect; smooth; some gland-tipped cilia. Color—between Lettuce Green, Plate V (Ridgway) and Spinach Green, Plate V (Ridgway), shaded with near Deep Corinthian Red, Plate XXVII (Ridgway) on side exposed to sun.

*Before calyx breaks.* — Size — medium. Form—medium length; ovoid; with foliaceous appendages, some tomentum, and very few gland-tipped cilia on the surface of the bud; usually with stout, much-cut foliaceous parts extending beyond the tip of the bud equal to ¼ to ½ or sometimes more of its length.

*As calyx breaks.*—Color—between Cardinal Red, Plate 822, page 168 (Wilson) and Chrysanthemum Crimson, Plate 824/1, page 169 (Wilson).

*Sepals.*—Inner surface—with fine, woolly tomentum. Margins—margins of alternate sepals with wooly tomentum; others lined with stipitate glands.

*As first petal opens.*—Size—average. Form—medium length; urn-shaped. Color—outside—between Cardinal Red, Plate 822/2, page 168 (Wilson) and Cardinal Red, Plate 822/3, page 168 (Wilson), with small area at base of petal near attachment near Aureolin, Plate 3/3, page 3 (Wilson). Inside—between Currant Red, Plate 821, page 167 (Wilson) and Cardinal Red, Plate 822/1, page 168 (Wilson), with small area at base of petal near attachment near Aureolin, Plate 3/3, page 3 (Wilson).

*Opening.*—Opens up well; is not retarded from opening by cold, hot, wet or dry weather.

Bloom:

*Size, when fully open.*—Average; 3 inches to 4 inches.

*Petalage.*—Double; from 35 to 40 petals, plus 12 to 16 petaloids; arranged regularly.

*Form.*—High-centered at first; becoming flat and open later; petals being at first somewhat flat-cupped, with lateral margins reflexed for ½ of length of upper half of petal, and with apex sometimes reflexed for ¼ of petal length; becoming flat later at maturity with lateral margins reflexed usually for ¾ of upper part of petal, and also with apex sometimes reflexed for ½ of petal length.

Petals:

*Texture.*—Thick; leathery; with inside velvety and outside satiny.

*Shape.*—Outside—obovate, with apex somewhat flat and very rarely with 1 notch. Intermediate—obovate, with apex rounded and very rarely with 1 notch. Inside—obovate, with apex rounded and rarely with 1 or 2 notches.

This description of a newly opened flower was made from a rose grown outdoors in the month of October, at Ontario, California:

*Color.*—Outside petal: outside surface—between Currant Red, Plate 821/3, page 167 (Wilson) and Cardinal Red, Plate 822/3, page 168 (Wilson), with small area at base of petal near attachment near Aureolin, Plate 3/3, page 3 (Wilson); inside surface—between Currant Red, Plate 821/1, page 167 (Wilson) and Cardinal Red, Plate 822/1, page 168 (Wilson), with small area at base of petal near attachment near Aureolin, Plate 3/3, page 3 (Wilson). Intermediate petal: outside surface—between Currant Red, Plate 821/3, page 167 (Wilson) and Cardinal Red, Plate 822/3, page 168 (Wilson), with small area at base of petal near attachment near Aureolin, Plate 3/3, page 3 (Wilson); inside surface—between Currant Red, Plate 821/1, page 167 (Wilson) and Cardinal Red, Plate 822/1, page 168 (Wilson), with small area at base of petal near attachment near Aureolin, Plate 3/3, page 3 (Wilson). Inner petal: outside surface—between Cardinal Red, Plate 822/1, page 168 (Wilson) and Cardinal Red, Plate 822/2, page 168 (Wilson), with small area at base of petal near attachment near Aureolin, Plate 3/3, page 3 (Wilson); inside surface—near Cardinal Red, Plate 822, page 168 (Wilson), with small area at base of petal near Aureolin, Plate 3/3, page 3 (Wilson).

This description was made from a rose that was open for three days outdoors in the month of October, at Ontario, California:

*Color.*—Outside petal: outside surface—between Rose Red, Plate 724, page 158 (Wilson) and Cardinal Red, Plate 822/3, page 168 (Wilson), with small area at base of petal near attachment near Aureolin, Plate 3/3, page 3 (Wilson); inside surface—between Cardinal Red, Plate 822/1, page 168 (Wilson) and Cardinal Red, Plate 822/2, page 168 (Wilson), with small area at base of petal near attachment near Aureolin, Plate 3/3, page 3 (Wilson). Inside petal: outside surface—near Cardinal Red, Plate 822/3, page 168 (Wilson), with small area at base of petal near attachment near Aureolin, Plate 3/3, page 3 (Wilson); inside surface—between Currant Red, Plate 821/2, page 167 (Wilson) and Cardinal Red, Plate 822/1, page 168 (Wilson), with small area at base of petal near attachment near Aureolin, Plate 3/3, page 3 (Wilson).

*General color effect.*—Newly opened flower—between Currant Red, Plate 821/1, page 167 (Wilson) and Cardinal Red, Plate 822, page 168 (Wilson). 3 days open—between Currant Red, Plate 821/2, page 167 (Wilson) and Cardinal Red, Plate 822/2, page 168 (Wilson), with small area at base of petal near attachment near Aureolin, Plate 3/3, page 3 (Wilson).

*Behavior.*—Drop off cleanly; not particularly affected by cold, hot, wet or dry weather.

*Flower longevity.*—On bush in garden—4 to 5 days in October. Cut roses grown outdoors kept at living-room temperatures—5 days in October.

*Reproductive organs*

Stamens: Average number; arranged regularly about pistils; a few mixed with petaloids.

Filaments: Short to medium length; 3 to 7 mm. in length; most with anthers. Color—near Sulphur Yellow, Plate 1/3, page 1 (Wilson), shaded somewhat with near Carmine, Plate 21/3, page 21 (Wilson) on upper ½ of filament.

Anthers: Medium size; all open approximately at once. Color—upper side—margins near Indian Yellow, Plate 6/2, page 6 (Wilson); remainder near Amber Yellow, Plate 505/3, page 132 (Wilson); under side—margins near Indian Yellow, Plate 6/2, page 6 (Wilson); remainder near Amber Yellow, Plate 505/3, page 132 (Wilson).

Pollen: Moderate in quantity. Color—between Indian Yellow, Plate 6/2, page 6 (Wilson) and Saffron Yellow, Plate 7/2, page 7 (Wilson).

Pistils: Few to average number; approximately 45 in number.

Styles: Moderately even; average length; 5 to 10 mm. long; average caliper; bunched. Color—upper ⅓ to ½ near Crimson, Plate 22, page 22 (Wilson); lower ½ to ¾ near Uranium Green, Plate 63/3, page 63 (Wilson).

Stigma: Color—near Aureolin, Plate 3/3, page 3 (Wilson).

Ovaries: Few enclosed in but most protruding from calyx.

Hips: Average length; globular; smooth; walls thick and fleshy. Color (¾ mature)—between Javel Green, Plate V (Ridgway) and Lettuce Green, Plate V (Ridgway).

Sepals: Permanent; long; recurved. Color—inside—between Chromium Green, Plate XXXII (Ridgway) and Deep Dull Yellow Green, Plate XXXII (1) (Ridgway), masked by white woolly tomentum; outside—between Deep Dull Yellow Green, Plate XXXII (1) (Ridgway) and Dark Dull Yellow Green, Plate XXXII (Ridgway), shaded slightly with near Dark Corinthian Purple, Plate XXXVIII (Ridgway).

Seeds: Few; medium size; 3 to 7 in number.

*Plant*

Foliage:

*Leaves.*—Compound of usually 5 to 7 leaflets; abundant; medium size to large; moderately heavy; leathery and glossy.

*Leaflets.*—Shape—ovoid, with acute apex and round base. Margin—doubly serrate.

*Color.*—Mature: upper surface—between Deep Dull Yellow-Green, Plate XXXII (1) (Ridgway) and Dark Dull Yellow Green, Plate XXXII (Ridgway); under surface—near Chromium Green, Plate XXXII (Ridgway). Young: upper surface—near Cerro Green, Plate V (Ridgway), very heavily shaded with near Neutral Red, Plate XXXVIII (Ridgway); under surface—between Corinthian Purple, Plate XXXVIII (Ridgway) and Neutral Red, Plate XXXVIII (Ridgway).

*Rachis (the supporting stem of the compound leaf).*—Average size. Upper side—grooved, with some hairs and some stipitate glands on edges. Under side—prickly and with few stipitate glands.

*Stipules.*—Medium length; narrow to medium width; with medium length points turning out at an angle of about 45°.

*Disease.*—More than average resistance to mildew, as compared with other varieties grown under comparable cultural conditions at Ontario, California.

Growth:

*Habit.*—Bushy; upright; much-branched.

*Growth.*—Very vigorous.

*Canes.*—Heavy.

*Main stems.*—Color—between Calla Green, Plate V (Ridgway) and Oil Green, Plate V (Ridgway). Large prickles—many; medium length; hooked slightly downward; with medium length to moderately long, narrow base. Color—between Tawny, Plate XV (Ridgway) and Russet, Plate XV (Ridgway). Small prickles—very few. Color—between Tawny, Plate XV (Ridgway) and Russet, Plate XV (Ridgway). Hairs—none.

*Branches.*—Color—near Oil Green, Plate V (Ridgway). Large prickles—several to many; medium length; hooked slightly downward; with medium length to moderately long, narrow base. Color—near Tawny, Plate XV (Ridgway). Small prickles—several. Color—near Tawny, Plate XV (Ridgway). Hairs—none.

*New shoots.*—Color—near Courge Green, Plate XVII (Ridgway), shaded somewhat with near Deep Corinthian Red, Plate XXVII (Ridgway). Large prickles—several; medium length; hooked very slightly downward; with medium length to moderately long, narrow base. Color—near Light Dull Green-Yellow, Plate XVII (Ridgway), heavily shaded with near Hydrangea Red, Plate XXVII (Ridgway). Small prickles—several. Color—near Light Dull Green-Yellow, Plate XVII (Ridgway), heavily shaded with near Hydrangea Red, Plate XXVII (Ridgway). Hairs—none.

I claim:

A new and distinct variety of rose plant of the hybrid tea class, substantially as herein shown and described, characterized particularly as to novelty by its cluster blooming habit, by its relatively long individual flowering stems, by the relatively large size of its flowers, by its abundance of bloom production throughout the growing season, by the distinctive color of its flowers, by the good petal substance of its flowers with attendant long-lasting quality thereof, and by its abundance of relatively large, dark green glossy foliage.

No references cited.